(12) United States Patent
Solomon et al.

(10) Patent No.: US 8,361,458 B2
(45) Date of Patent: *Jan. 29, 2013

(54) METHOD AND FILAMENTOUS PHAGE FOR TREATING INFLAMMATION ASSOCIATED WITH AMYLOID DEPOSITS AND BRAIN INFLAMMATION INVOLVING ACTIVATED MICROGLIA

(75) Inventors: Beka Solomon, Herzliya (IL); Orna Goren, Shoham (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/966,786

(22) Filed: Dec. 13, 2010

(65) Prior Publication Data

US 2011/0142803 A1 Jun. 16, 2011

Related U.S. Application Data

(63) Continuation of application No. 11/815,294, filed as application No. PCT/US2006/003291 on Jan. 31, 2006, now Pat. No. 7,867,487.

(60) Provisional application No. 60/648,383, filed on Feb. 1, 2005.

(51) Int. Cl.
*A61K 38/00* (2006.01)

(52) U.S. Cl. .................................. 424/93.2

(58) Field of Classification Search ............ None
See application file for complete search history.

(56) References Cited

FOREIGN PATENT DOCUMENTS

WO 03059386 7/2003

OTHER PUBLICATIONS

Gocayne et al. Primary structure of rat cardiac fi-adrenergic and muscarinic holinergic receptors obtained by automated DNA sequence analysis: Further evidence for a multigene family. Proc. Natl. Acad. Sci., 1987, vol. 84, pp. 8296-8300.*
El-Sheikh et al. A Novel Vascular Endothelial Growth Factor Heparin-binding Domain Substructure Binds to Glycosaminoglycans in Vivo and Localizes to Tumor Microvascular Endothelium. Cancer Research, 2002, vol. 62, pp. 7118-7123.*
Banks WA and Kastin AJ, "Bidirectional passage of peptides across the blood-brain barrier" Progress in Brain Research, 91:139-148 (1992).
Bard et al., "Peripherally administered antibodies against amyloid β-peptide enter the central nervous system and reduce pathology in a mouse model of Alzheimer disease" Nat. Med., 6:916-919 (2000).
Caughey et al., "Secondary Structure Analysis of the Scrapie-Associated Protein PrP 27-30 in Water by Infrared Spectroscopy", Biochemistry, 30:7672-7680 (1991).
Chartier et al., "Early-Onset Alzheimer's Disease Caused by Mutations at Codon 717 of the β-amyloid precursor protein gene", Nature, 353:844-846 (1991).
Chou KJ and Donovan MD, "Distribution of Antihistamines Into the CSF Following Intranasal Delivery", Biopharm Drug Dispos., 18:335-346 (1997).
De Gioia et al, "Conformational Polymorphism of the Amyloidogenic and Neurotoxic Peptide Homologous to Residues 106-126 of the Prion Protein" J. Biol Chem., 269:7859-7862 (1994).
Draghia et al., "Gene delivery into the central nervous system by nasal instillation in rats", Gene Therapy, 2:418-423 (1995).
Forloni et al., "Neurotoxicity of a prion protein fragment", Nature, 362:543-546 (1993).
Frenkel et al., "N-terminal EFRH sequence of Alzheimer's b-amyloid peptide represents the epitope of its anti-aggregating antibodies", Journal of Neuroimmunology, 88:85-90 (1998).
Frenkel D and Solomon B, "Filamentous phage as vector-mediated antibody delivery to the brain", PNAS, 99:5675-5679 (2002).
Gajdusek, D.C., "Unconventional Viruses and the Origin and Disappearance of Kuru", Science, 197:943-960 (1977).
Gazit, E, "Mechanistic Studies of the Process of Amyloid Fibrils Formation by the Use of Peptide Fragments and Analogues: Implications for the Design of Fibrillization Inhibitors", Curr. Med. Chem., 9:1725-1735 (2002).
Goate et al., "Segregation of a Missense Mutation in the Amyloid Precursor Protein Gene with familial Alzheimer's disease", Nature, 349:704-706 (1991).
Greenwood et al., "Multiple Display of Foreign Peptides on a Filamentous Bacteriophage", J. Mol. Biol., 220:821-827 (1991).
Griffith et al., "Filamentous Bacteriophage Contract into Hollow Spherical Particles upon Exposure to a Chloroform-Water Interface", Cell, 23:747-753 (1981).
Hardy, J., "Amyloid, the presenilins and Alzheimer's disease", TINS, 20:154-159 (1997).
Hart et al., "Cell Binding and Internalization by Filamentous Phage Displaying a Cyclic Arg-Gly-Asp-containing Peptide", J. Biol. Chem., 269:12468-12474 (1994).
Horiuchi M and Caughey B., "Specific binding of normal prion protein to the scrapie form via a localized domain initiates its conversion to the protease-resistant state", EMBO J., 18:3193-3203 (1999).
Kanyo et al., "Antibody Binding Defines a Structure for an Epitope that Participates in the PrPC→PrPSc Conformational Change", J, Mol, Biol., 293:855-863 (1999).
LeVine H., "Thioflavine T interaction with synthetic Alzheimer's disease β-amyloid peptides: Detection of amyloid aggregation in solution", Protein Science, 2:404-410 (1993).
Lin at al., "Selection of Specific Phage from Display Libraries: Monoclonal Antibody Against VCS M13 Helper Phage Coat Protein III (gIIIp)", Hybridoma, 18:257-261 (1999).
Maggio JE and Mantyh PW, "Brain Amyloid—A Physicochemical Perspective", Brain Pathology, 6:147-162 (1996).
Marvin DA and Hale RD , "Molecular Models and Structural Comparisons of Native and Mutant Class I Filamentous Bacteriophages Ff (fd, fl, M13), If1 and IKe", J. Mol. Biol., 235:260-286 (1994).
Marvin DA, "Filamentous phage structure, infection and assembly", Current Opinion in Structural Biology, 8:105-158 (1998).

(Continued)

*Primary Examiner* — Deborah Crouch
(74) *Attorney, Agent, or Firm* — Browdy and Neimark, PLLC

(57) ABSTRACT

Filamentous bacteriophage which does not display an antibody or a non-filamentous bacteriophage antigen on its surface is used to inhibit or treat brain inflammation associated with amyloid deposits and/or involving activated microglia, to inhibit the formation of amyloid deposits, and to disaggregate pre-formed amyloid deposits.

16 Claims, 6 Drawing Sheets

OTHER PUBLICATIONS

Mathison et al., "Nasal Route for Direct Delivery of Solutes to the Central Nervous System: Fact or Fiction?", J. Drug Target., 5:415-441 (1998).

McCafferty et al., "Phage Antibodies: Filamentous Phage Displaying Antibody Variable Domains", Nature, 348:552-554 (1990).

Medori et al., "Fatal Familial Insomnia, A Prion Disease With a Mutation at Codon 178 of the Prion Protein Gene", N. Engl. J. Med., 326:444-449 (1992).

Monaci et al., "Phage as gene delivery vectors", Curr. Opin, Mol. Ther., 3:159-169 (2001).

Mullen et al., "A pathogenic mutation for probable Alzheimer's disease in the APP gene at the N-terminus of β-amyloid", Nature Genet., 1:345-347 (1992).

Murrell et al., "A mutation in the amyloid precursor protein associated with hereditary Alzheimer's disease", Science, 254:97-101 (1991).

Pan et al., "Conversion of a-helices into β-sheets features in the formation of the scrapie prion proteins", PNAS USA, 90:10962-10966 (1993).

Peretz et al., "A Conformational Transition at the N Terminus of the Prion Protein Features in Formation of the Scrapie Isoform", J. Mol. Biol., 273:614-622 (1997).

Pike et al., "Amino-terminal Deletions Enhance Aggregation of β-Amyloid Peptides in Vitro", J. Biol. Chem., 270:23895-23898 (1995).

Roberts LM and Dunker AK, "Structural Changes Accompanying Chloroform-Induced Contraction of the Filamentous Phage fd", Biochemistry, 32:10479-10488 (1993).

Rodi DJ and Makowski L, "Phage-display technology—finding a needle in a vast molecular haystack", Current Opinion in Biotechnology, 10:87-93 (1999).

Scott JK and SMith GP, "Searching for peptide ligands with an epitope library", Science, 249:386-639 (1990).

Selvaggini et al., "Molecular Characteristics of a Protease-Resistant, Amyloidogenic and Neurotoxic Peptide Homologous to Residues 106-126 of the Prion Protein", Biochem. Biophys. Res. Comm., 1994:1380-1386 (1993).

Silen JL and Agard DA, "The α-lytic protease pro-region does not require a physical linkage to activate the protease domain in vivo", Nature, 341:462-464 (1989).

Solomon et al., "Monoclonal antibodies inhibit in vitro fibrillar aggregation of the Alzheimer β-amyloid peptide", PNAS USA, 93:452-465 (1998).

Solomon et al., "Disaggregation of Alzheimer β-amyloid by site-directed mAb", PNAS USA, 94:4109-4112 (1997).

Tagliavini et al., "Synthetic peptides homologous to prion protein residues 106-147 form amyloid-like fibrils in vitro", PNAS USA, 90:9678-9682 (1993).

Wilesmith DR and Wells GAH, "Bovine Spongiform Encephalopathy", Curr. Top. Microbiol. Immunol., 172:21-38 (1991).

Wilson DR and Finlay BB, "Phage display: Applications, innovations, and issues in phage and host biology", Can J. Microbiol., 44:313-329 (1998).

Young et al., "Selective amylin antagonist suppresses rise in plasma lactate after intravenous glucose in the rat: Evidence for a metabolic role of endogenous amylin", FEBS Lett., 343:237-241 (1994).

Lichtlen et al., Antibody-based approaches in Alzheimer's research: safety, pharmacokinetics, metabolism, and analytical tools, J. Neurochem. 104:859-874 (2008).

Games et al., Alzheimer-type neuropathology in transgenic mice overexpressing V717F β-amyloid precursor protein, Nature 373:523-527 (1995).

Holmes et al., Long-term effects of Aβ42 immunisation in Alzheimer's disease: follow-up of a randomised, placebo-controlled phase I trial, Lancet 372:216-223, 2008.

Rinne et al., 11C-PiB PET assessment of change in fibrillar amyloid-β load in patients with Alzheimer's disease treated with bapineuzumab: a phase 2, double-blind, placebo-controlled, ascending-dose study, online publication Mar. 1, 2010, at www.thelancet.com/neurology).

Molenaar et al., Uptake and processing of modified bacteriophage M13 in Mice: Implications for Phage Display. Virology, 293:182-191 (2002).

Rasched et al., Ff Coliphages: Structural and Functional Relationships, Microbiological Reviews, 50(4):401-427 (1986).

Marvin et al., Filamentous Bacterial Viruses, Bacteriological Reviews, 33(2):172-209 (1969).

Zhang et al., Advance in Bacteriophage therapy, Foreign Medical Sciences (Microbiology), (1):29-31, 38 (2001).

Frenkel et al., Reduction of β-amyloid plaques in brain of transgenic mouse model of Alzheimer's disease by EFRH-phase immunization, Vaccine, 21(11-12):1060-1065 (2003).

Weisehan et al., Selection of D-amino acid peptides that bind to Alzheimer's disease amyloid peptide A1-42 by mirror image phase display, Chem. Biochem., 4(8):748-753 (2003).

Lundin et al., Generation of microglia specific reagents from phage displayed peptide libraries, J. of Immunological Methods, 278(1-2):235-247 (2003).

Amyloid entry from en.wikipedia.org as printed out on Oct. 11, 2011.

Dimant et al., Modulation effect of filamentous phage on alpha-synuclein aggregation, Biochemical and Biophysical Research Communications, 383:491-496 (2009).

Petsch et al., Endotoxin removal from protein solutions, Journal of Biotechnology, 76:97-119 (2000).

Tremblay et al., Complete genomic sequence of the lytic Bacteriophage DT1 of *Streptococcus thermophilus*, Virology, 255:63-76 (1999).

Alisky et al, Bacteriophages show promise as antimicrobial agents, Journal of Infection, 36:5-15 (1998).

Dimant et al., Filamentous phages reduce alpha-synuclein oiigomerization in the membrane fraction of SH-SY5Y cells, Neurodegenerative Dis, 7:203-205 (2010).

Krag et al., Phage-displayed random peptide libraries in mice: toxicity after serial panning, Cancer Chemother Pharmacol., 50:325-332 (2002).

Sulakvelidze et al., Bacteriophage therapy, Antimicrobial Agents and Cehmotherapy, 649-659 (Mar. 2001).

Sipe et al., Review: History of the Amyloid Fibril, J. Struct. Biol. 130:88-98 (2000).

\* cited by examiner

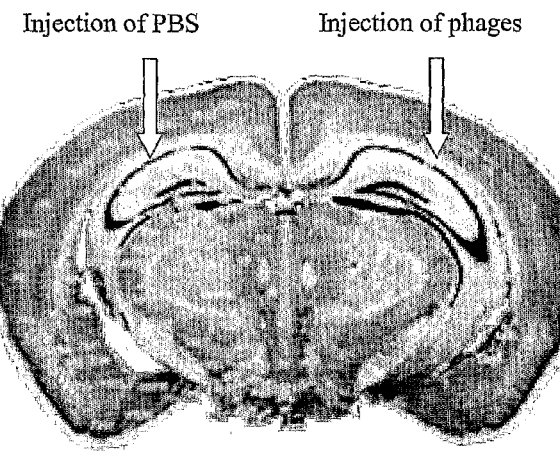
FIG. 1
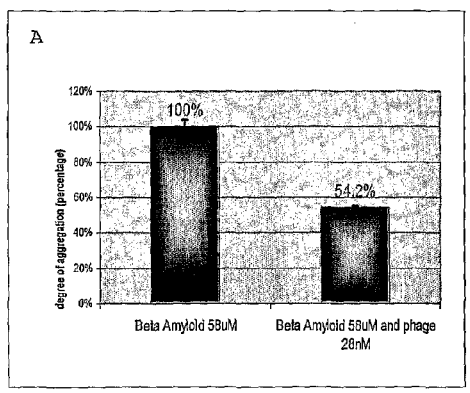 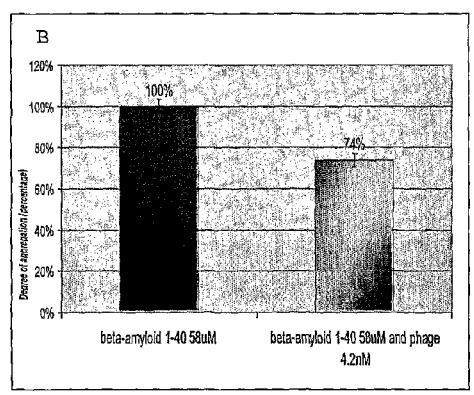
FIG. 2A  FIG. 2B

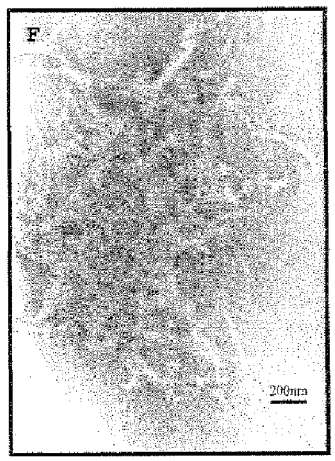 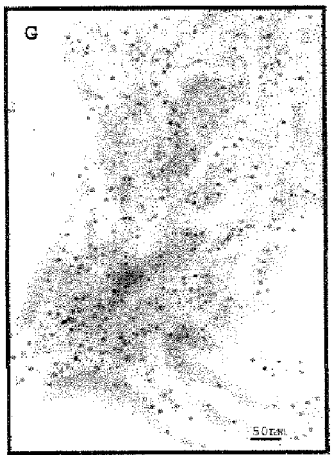 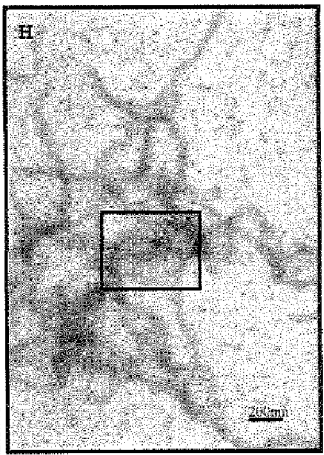
FIG. 3F　　　　　FIG. 3G　　　　　FIG. 3H
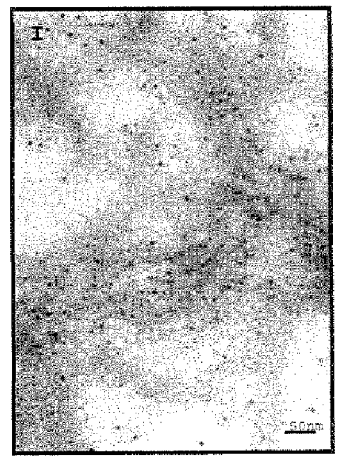 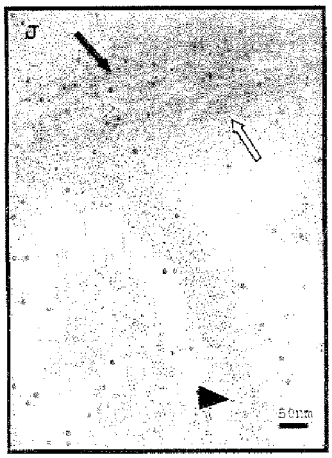 
FIG. 3I　　　　　FIG. 3J　　　　　FIG. 3K

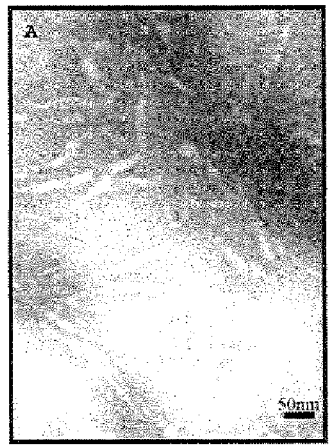 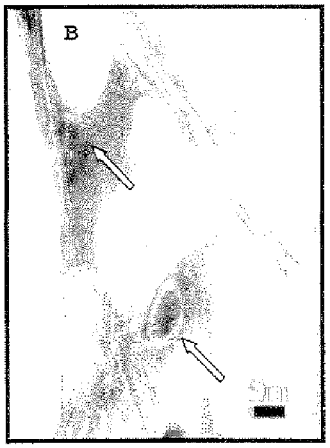 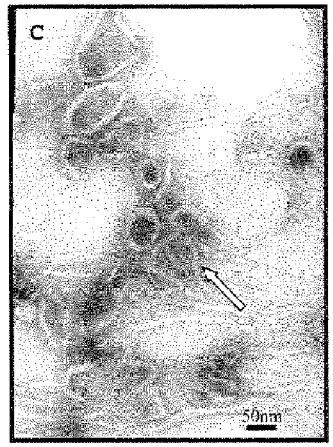
FIG. 4A    FIG. 4B    FIG. 4C
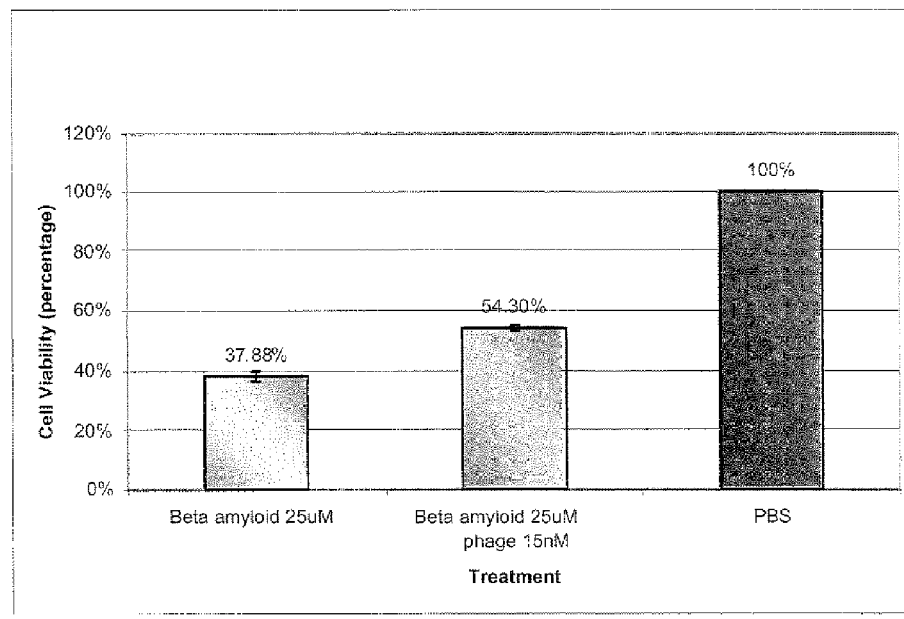
FIG. 5A

METHOD AND FILAMENTOUS PHAGE FOR TREATING INFLAMMATION ASSOCIATED WITH AMYLOID DEPOSITS AND BRAIN INFLAMMATION INVOLVING ACTIVATED MICROGLIA

CROSS-REFERENCE TO RELATED APPLICATIONS

This application is a continuation of application Ser. No. 11/815,294, which is a 371 national stage application of PCT/US06/03291, filed Jan. 31, 2006, which claims priority from U.S. provisional application No. 60/648,383, filed Feb. 1, 2005, the entire contents of which applications are hereby incorporated by reference.

BACKGROUND OF THE INVENTION

1. Field of the Invention

The invention relates to inhibiting amyloid deposit formation and dissolving pre-formed amyloid deposits and to methods and pharmaceutical compositions for treating brain inflammation and for treating inflammation associated with amyloid or amyloid-like deposits within the brain and elsewhere in the body.

2. Description of the Related Art

Plaque forming diseases are characterized by the presence of amyloid plaques deposits in the brain as well as neuronal degeneration. Amyloid deposits are formed by peptide aggregated into an insoluble mass. The nature of the peptide varies in different diseases but in most cases, the aggregate has a beta-pleated sheet structure and stains with Congo Red dye. In addition to Alzheimer's disease (AD), which includes early onset Alzheimer's disease, late onset Alzheimer's disease, and presymptomatic Alzheimer's disease, other diseases characterized by amyloid deposits are, for example, SAA amyloidosis, hereditary Icelandic syndrome, multiple myeloma, and prion diseases. The most common prion diseases in animals are scrapie of sheep and goats and bovine spongiform encephalopathy (BSE) of cattle (Wilesmith and Wells, 1991). Four prion diseases have been identified in humans: (i) kuru, (ii) Creutzfeldt-Jakob Disease (CJD), (iii) Gerstmann-Streussler-Sheinker Disease (GSS), and (iv) fatal familial insomnia (FFI) (Gajdusek, 1977; and Tritschler et al. 1992).

Prion diseases involve conversion of the normal cellular prion protein (PrPC) into the corresponding scrapie isoform (PrPSc). Spectroscopic measurements demonstrate that the conversion of PrPC into the scrapie isoform (PrPSc) involves a major conformational transition, implying that prion diseases, like other amyloidogenic diseases, are disorders of protein conformation. The transition from PrPC to PrPSc is accompanied by a decrease in $\alpha$-helical secondary structure (from 42% to 30%) and a remarkable increase in $\beta$-sheet content (from 3% to 43%) (Caughey et al, 1991; and Pan et al, 1993). This rearrangement is associated with abnormal physiochemical properties, including insolubility in non-denaturing detergents and partial resistance to proteolysis. Previous studies have shown that a synthetic peptide homologous with residues 106-126 of human PrP (PrP106-126) exhibits some of the pathogenic and physicochemical properties of PrPSc (Selvaggini et al, 1993; Tagliavini et al, 1993; and Forloni et al, 1993). The peptide shows a remarkable conformational polymorphism, acquiring different secondary structures in various environments (De Gioia et al, 1994). It tends to adopt a $\beta$-sheet conformation in buffered solutions, and aggregates into amyloid fibrils that are partly resistant to digestion with protease. Recently, the X-ray crystallographic studies of a complex of antibody 3F4 and its peptide epitope (PrP 104-113) provided a structural view of this flexible region that is thought to be a component of the conformational rearrangement essential to the development of prion disease (Kanyo et al, 1999). The identification of classes of sequences that participate in folding-unfolding and/or solubilization-aggregation processes may open new direction for the treatment of plaque forming disease, based on the prevention of aggregation and/or the induction of disaggregation (Silen and Agard, 1989; Frenkel et al, 1998; Horiuchi and Caughey, 1999).

Alzheimer's disease (AD) is a progressive disease resulting in senile dementia. Broadly speaking, the disease falls into two categories: late onset, which occurs in old age (typically above 65 years) and early onset, which develops well before the senile period, e.g., between 35 and 60 years. In both types of the disease, the pathology is similar, but the abnormalities tend to be more severe and widespread in cases beginning at an earlier age. The disease is characterized by two types of lesions in the brain, senile plaques and neurofibrillary tangles. Senile plaques are areas of disorganized neutrophils up to 150 mm across with extracellular amyloid deposits at the center, visible by microscopic analysis of sections of brain tissue. Neurofibrillary tangles are intracellular deposits of tau protein consisting of two filaments twisted about each other in pairs.

The principal constituent of the senile plaques is a peptide termed amyloid beta (A$\beta$) or beta-amyloid peptide ($\beta$AP or) $\beta$A). The amyloid beta peptide is an internal fragment of 39-43 amino acids of a precursor protein termed amyloid precursor protein (APP). Several mutations within the APP protein have been correlated with the presence of Alzheimer's disease (Goate et al, (1991), valine717 to isoleucine; Chartier Harlan et al, (1991), valine717 to glycine; Murrell et al, (1991), valine717 to phenylalanine; Mullan et al, (1992), a double mutation, changing lysine595-methionine596 to asparagine595-leucine596).

Such mutations are thought to cause Alzheimer's disease by increased or altered processing of APP to beta-amyloid, particularly processing of APP to increased amounts of the long form of beta-amyloid (i.e., A$\beta$1-42 and A$\beta$1-43). Mutations in other genes, such as the presenilin genes, PS1 and PS2, are thought indirectly to affect processing of APP to generate increased amounts of long form beta-amyloid (see Hardy, TINS 20, 154, 1997). These observations indicate that beta-amyloid, and particularly its long form, is a causative element in Alzheimer's disease.

Other peptides or proteins with evidence of self aggregation are also known, such as, but not limited to, amylin (Young et al, 1994); bombesin, cerulein, cholecystokinin octapeptide, eledoisin, gastrin-related pentapeptide, gastrin tetrapeptide, somatostatin (reduced), substance P; and peptide, luteinizing hormone releasing hormone, somatostatin N-Tyr (Banks and Kastin, 1992).

Publications on amyloid fibers indicate that cylindrical $\beta$-sheets are the only structures consistent with some of the x-ray and electron microscope data, and fibers of Alzheimer A$\beta$ fragments and variants are probably made of either two or three concentric cylindrical $\beta$-sheets (Perutz et al., 2002). The complete A$\beta$ peptide contains 42 residues, just the right number to nucleate a cylindrical shell; this finding and the many possible strong electrostatic interactions in $\beta$-sheets made of the A$\beta$ peptide in the absence of prolines account for the propensity of the A$\beta$ peptide to form the extracellular amyloid plaques found in Alzheimer patients. If this interpretation is correct, amyloid consists of narrow tubes (nanotubes) with a central water-filled cavity. Reversibility of amyloid plaque growth in-vitro suggests steady-state equilibrium between βA in plaques and in solution (Maggio and Mantyh, 1996). The dependence of βA polymerization on peptide-peptide interactions to form a β-pleated sheet fibril, and the stimulatory influence of other proteins on the reaction, suggest that amyloid formation may be subject to modulation. Many attempts have been made to find substances able to interfere with amyloid formation. Among the most investigated compounds are antibodies, peptide composed of beta-breaker amino acids like proline, addition of charged groups to the recognition motif and the use of N-methylated amino-acid as building blocks (reviewed by Gazit, 2002).

Cyclic peptides made of alternate D and L residues form such nanotubes that kill bacteria by inserting themselves into membranes and depolarizing them (Perutz et al., 2002). There is some suggestion that some amyloid fibers might be conductors and kill cells by the same mechanism.

Aromatic compounds such as congo red that can insert themselves into gaps between helical turns might destabilize the cylindrical shells and initiate this process, but prevention would be more effective and probably easier to achieve (Perutz et al., 2002).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for inhibiting or treating inflammation associated with amyloid deposits within the brain and elsewhere in the body and brain inflammation involving activated microglia. The method involves administering to a patient in need thereof an effective amount of a wild-type filamentous bacteriophage or a filamentous bacteriophage which does not display an antibody or a non-filamentous bacteriophage antigen on its surface.

The present invention also provides a pharmaceutical composition containing an effective amount of the filamentous bacteriophage as the active ingredient.

The present further provides methods for inhibiting the formation of amyloid deposits or for disaggregating pre-formed amyloid deposits by contacting filamentous bacteriophage with plaque forming peptides or pre-formed amyloid deposits.

BRIEF DESCRIPTION OF THE DRAWINGS

FIG. 1 is a schematic illustration of a cross-section of the brain showing intracranial application of phage/PBS to hAPP transgenic mice. Phages were injected intracerebrally to five transgenic mice. To the contralateraly hemisphere, PBS was injected. The mice were sacrificed after 1 hour, 2 days and 3 days. Their brain were cut to 5 μm sections, and are being stained with Thioflavine-S to evaluate their plaque load.

FIGS. 2A and 2B are graphs showing disaggregation (FIG. 2A) and prevention (FIG. 2B) of β-amyloid 1-40 aggregation by filamentous phage using the ThT assay. In FIG. 2A (disaggregation test), β-amyloid (54 μM) was incubated for 21 days alone. On the $21^{th}$ day, different phage concentrations were added and incubated overnight. In FIG. 2B (prevention test) β-amyloid (58 μM) was incubated either alone or with filamentous phage for 7 days, then the samples were added to ThT solution and amyloid content was measured by spectrof-luorimeter. Amyloid content was measured using Thioflavin-T which binds to amyloid fibrils and its fluorescent emission was detected at 485 nm wavelength.

FIGS. 3A-3K are electron micrographs of β-amyloid which was incubated in the absence or presence of filamentous phage (magnification ×100K). FIG. 3A: β-amyloid 97 μM in PBS in the absence of phage. β-amyloid was stained with mouse monoclonal antibody 10D5 followed by goat anti mouse 12 mn gold conjugated antibody. FIGS. 3B-3C: β-amyloid 97 μM incubated with 0.5 nM ($1 \times 10^{10}$) phages. β-amyloid was stained with mouse monoclonal antibody 10D5 and 2nd antibody conjugated to 12 mn gold particle. The phage was labeled with polyclonal rabbit anti-phage sera, followed by goat anti-rabbit 6 nm gold conjugated antibody. No signal of those second antibodies was observed in samples containing no phage or no $1^{st}$ antibodies. FIG. 3D: Filamentous phage (fd) ($1 \times 10^{10}$ phages) was stained with rabbit polyclonal sera. The 2nd antibody was conjugated to 6 nm gold particle. FIG. 3E: Filamentous phage near beta amyloid. The peptide probably enhances the phage degradation as the scattered labeling with anti-phage antibody shows (arrow). This labeling is absent when phage is incubated alone (sample D). FIGS. 3F-3G; β-amyloid alone after 10 days of incubation at 37° C. (magnification: F-×30K, G-×100K). FIGS. 3H-3I: β-amyloid was incubated alone for 10 days, on the 10th day filamentous phages were added for another 16 hours (H-×30K, I-×100K enlargement of H). FIGS. 3J-3K: Interface between amyloid fibril and filamentous phage. The phages are organized along the fibril axis (×100K).

FIGS. 4A-4C are electron micrographs where spherical phages were added to preaggregated β-amyloid and incubated together overnight. β-amyloid with spherical phages (FIGS. 4A and 4B). Spherical phage alone (FIG. 4C) (magnification ×100K).

FIGS. 5A-5C are graphs showing inhibition of β-amyloid toxicity to LAN-1 cells by filamentous phage using the MTT assay. For the prevention assay in FIG. 5A, phages were added to 25 μM β-amyloid at molar ratios of 1760:1, βA/phage. The mixtures were added to the cells. The viability percentages are related to cell viability in the absence of β-amyloid (treatment-PBS), which is considered to be 100%. In FIGS. 5B and 5C, phage ability to protect against βA toxicity was measured using two preaggregated peptides: βA1-40 and βA17-42. Both peptides (βA 1-40 and βA 17-42) were incubated for 5 days at 37° C. On the $6^{th}$, day filamentous phage was added to the preaggregated peptides at a concentration of 1.2 nM and further incubated for 12 hours and then added to the cell line which was seeded in 96 well plate the day before. The cells were left to grow for another three days and then MTT was added. After 3 hours, extraction buffer was added and the plate was incubated overnight at 37° C. On the following day plate was read at 570 nm wavelength.

DETAILED DESCRIPTION OF THE INVENTION

Figure 3A:
Figure 3B:

β-Amyloid peptide (βA) is one of the two hallmarks of Alzheimer's disease. This peptide forms fibrillar toxic aggregates in brain tissue that can be dissolved only by strong denaturing agents. Since these neurotoxic properties are related to peptide aggregation forms, much effort has been invested in developing a therapeutic approach towards reducing or eliminating the extent of amyloid fibrillar deposition in the brain.

Under physiological conditions, a synthetic βA adopts an aggregated form and also shows a change from a neurite, promoting a neurotoxic effect on hippocampal neurons. Aggregation of βA has been shown to depend on pH, peptide concentration, temperature, and time of incubation.

The present inventors have surprisingly discovered that filamentous phage per se has the ability to prevent βA aggregation in vitro, as well as to dissolve already formed aggregates.

In the laboratory of the present inventors, filamentous phages M13, f1, and fd, which are well understood at both structural and genetic levels (Greenwood et al., 1991) were used. This laboratory first showed that filamentous bacteriophage exhibits penetration properties to the central nervous system while preserving both the inert properties of the vector and the ability to carry foreign molecules (Frenkel and Solomon, 2002).

Filamentous bacteriophages are a group of structurally related viruses which contain a circular single-stranded DNA genome. They do not kill their host during productive infection. The phages that infect *Escherichia coli* containing the F plasmids are collectively referred to as Ff bacteriophages. They do not infect mammalian cells.

The filamentous bacteriophages are flexible rods about 1 to 2 microns long and 6 nm in diameter, with a helical shell of protein subunits surrounding a DNA core. The two main coat proteins, protein pIII and the major coat protein pVIII, differ in the number of copies of the displayed protein. While pIII is presented in 4-5 copies, pVIII is found in ~3000 copies. The approximately 50-residue major coat protein pVIII subunit is largely alpha-helical and the axis of the alpha-helix makes a small angle with the axis of the virion. The protein shell can be considered in three sections: the outer surface, occupied by the N-terminal region of the subunit, rich in acidic residues that interact with the surrounding solvent and give the virion a low isoelectric point; the interior of the shell, including a 19-residue stretch of apolar side-chains, where protein subunits interact mainly with each other; and the inner surface, occupied by the C-terminal region of the subunit, rich in basic residues that interact with the DNA core. The fact that virtually all protein side-chain interactions are between different subunits in the coat protein array, rather than within subunits, makes this a useful model system for studies of interactions between alpha-helical subunits in a macromolecular assembly. The unique structure of filamentous bacteriophage enables its penetration into the brain, although it has a mass of approximately 16.3MD and may contribute to its ability to interfere with βA fibrillization since the phage structure resemble an amyloid fibril itself.

Considering the above, the present inventors have examined the ability of filamentous phage to interfere with the aggregation process of β-amyloid peptide and found that in vitro incubation of wild-type filamentous phage with β-amyloid peptide at different time intervals, with differing ratios, leads to prevention and/or disaggregation of β-amyloid. Moreover, the filamentous phage shows a protective effect on cell viability.

The most exciting data were obtained after incubation of the filamentous phage—β-amyloid fibrils with microglia cells grown on slides. If β-amyloid does activate microglia, the phage dissolves it without activating microglia. Phage technology provides a new and practically unlimited source of the anti-aggregating agent of β-amyloid, preventing the harmful effect of antibodies which might overactivate microglia via Fc receptors.

Bacteriophages have distinct advantages over animal viruses as gene and/or delivery vehicles. They are simple systems whose large-scale production and purification is very efficient and much cheaper than that of animal viral vectors. In addition, large segments of DNA can be efficiently packaged in phagemid vectors. Having evolved for prokaryotic infection, assembly and replication, bacteriophage can neither replicate in, nor show natural tropism for, mammalian cells. This minimizes the chances of non-specific gene delivery. Phage vectors are potentially much safer than viruses as they are less likely to generate a replication-competent entity in animal cells (Monaci et al., 2001).

The present invention provides a method for inhibiting or treating brain inflammation associated with amyloid deposits or involving activated microglia. In addition, the present method further inhibits or treats inflammation associated with amyloid deposits elsewhere in the body besides the brain, such as in the case of multiple myeloma and renal amyloidosis.

The present method involves introducing/administering to a patient in need thereof an effective amount of a wild-type filamentous bacteriophage or a filamentous bacteriophage which does not display an antibody or a non-filamentous bacteriophage antigen on its surface. The filamentous bacteriophage can be any filamentous bacteriophage such as M13, f1, or fd. Although M13 was used in the Example hereinbelow, any other filamentous bacteriophage is expected to behave and function in a similar manner as they have similar structure and as their genomes have greater than 95% genome identity.

When the method is used to inhibit or treat brain inflammation, the filamentous bacteriophage is preferably administered intranasally to introduce the active ingredient into the body of the recipient through an olfactory system of the recipient.

The present method not only inhibits the aggregation of protein into amyloid plaques or deposits in a plaque-forming disease, but also is effective in disaggregating pre-formed amyloid deposits such as βA fibrils.

The anti-aggregating or disaggregating property of the filamentous bacteriophage with respect to βA fibril formation or disaggregation can be measured by the well-known Thioflavin T (ThT) binding assay. Disrupted formation of βA fibril structure and disaggregation of preformed βA fibrils are indicated by a substantial decrease in ThT fluorescence.

For purposes of this specification and the accompanying claims, the terms "patient", "subject" and "recipient" are used interchangeably. They include humans and other mammals which are the object of either prophylactic, experimental, or therapeutic treatment.

For purposes of this specification and the accompanying claims, the terms "beta amyloid peptide" is synonymous with "β-amyloid peptide", "βAP", "βA", and "Aβ". All of these terms refer to a plaque forming peptide derived from amyloid precursor protein.

As used herein, "PrP protein", "PrP", "prion", refer to polypeptides which are capable under appropriate conditions, of inducing the formation of aggregates responsible for plaque forming diseases. For example, normal cellular prion protein (PrPC) is converted under such conditions into the corresponding scrapie isoform (PrPSc) which is responsible for plaque forming diseases such as, but not limited to, bovine spongiform encephalopathy (BSE), or mad cow disease, feline spongiform encephalopathy of cats, kuru, Creutzfeldt-Jakob Disease (CJD), Gerstmann-Straussler-Scheinker disease (GSS), and fatal familial insomnia (FFI).

As used herein, the term "disaggregating" refers to solubilization of aggregated proteins typically held together by non-covalent bonds.

The term "treating" is intended to mean substantially inhibiting, slowing or reversing the progression of a disease, substantially ameliorating clinical symptoms of a disease or substantially preventing the appearance of clinical symptoms of a disease.

Also as used herein, the term "plaque forming disease" refers to diseases characterized by formation of plaques by an aggregating protein (plaque forming peptide), such as, but not limited to, beta-amyloid, serum amyloid A, cystatin C, IgG kappa light chain or prion protein, in diseases such as, but not limited to, early onset Alzheimer's disease, late onset Alzheimer's disease, presymptomatic Alzheimer's disease, SAA amyloidosis, hereditary Icelandic syndrome, senility, multiple myeloma, and to prion diseases that are known to affect humans, such as for example, kuru, Creutzfeldt-Jakob disease (CJD), Gerstmann-Straussler-Scheinker disease (GSS), and fatal familial insomnia (FFI) and animals, such as, for example, scrapie and bovine spongiform encephalitis (BSE).

Because most of the amyloid plaques (also known as amyloid deposits) associated with the diseases described hereinabove are located within the brain, any proposed treatment modality must demonstrate an ability to cross the blood brain barrier (BBB) as well as an ability to dissolve amyloid plaques. Normally, the average size of molecules capable of penetrating the BBB is approximately 2 kDa.

An increasing body of evidence shows that olfactory deficits and degenerative changes in the central olfactory pathways are affected early in the clinical course of AD. Moreover, the anatomic patterns involved in AD suggest that the olfactory pathway may be the initial stage in the development of AD.

Olfactory receptor neurons are bipolar cells that reside in the epithelial lining of the nasal cavity. Their axons traverse the cribriform plate and project to the first synapse of the olfactory pathway in the olfactory bulb of the brain. This configuration makes them a highway by which viruses or other transported substances may gain access to the CNS across the BBB.

As previously shown, intranasal administration (Mathison et al, 1998; Chou et al, 1997; Draghia et al, 1995) enables the direct entry of viruses and macromolecules into the cerebrospinal fluid (CSF) or CNS.

Use of olfactory receptor neurons as a point of delivery for an adenovirus vector to the brain is reported in the literature. This method reportedly causes expression of a reporter gene in the brain for 12 days without apparent toxicity (Draghia et al, 1995).

Thus, according to a preferred embodiment of the present invention, the filamentous bacteriophage capable of disaggregating or preventing the formation of a polypeptide aggregate associated with a plaque forming disease or capable of inhibiting activation of microglia is delivered via this route to the brain.

As Aβ is produced continuously by cells in peripheral tissues which cross the blood brain barrier (BBB) leading to localized toxic effects in specific neuronal populations, intranasal administration of such a vehicle may also prevent the progression of the disease by minimizing the amount of peripheral Aβ available to form plagues.

A pharmaceutical preparation according to the present invention includes, as an active ingredient, a wild-type filamentous bacteriophage or a filamentous bacteriophage which does not display an antibody or a non-filamentous bacteriophage antigen on its surface. The pharmaceutical preparation can also be a mixture of different filamentous bacteriophages.

The preparation according to the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients, The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternatively, one may administer a preparation in a local rather than systemic manner, for example, via injection of the preparation directly into the brain of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in the context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, e.g., Fingl et al, in "The Pharmacological Basis of Therapeutics", Ch. 1 p. 1 (1975)).

Dosage amount and interval may be adjusted individually to provide plasma or brain levels of the filamentous bacteriophage which are sufficient to prevent aggregation or to disaggregate existing aggregates (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Having now generally described the invention, the same will be more readily understood through reference to the following example which is provided by way of illustration and is not intended to be limiting of the present invention.

EXAMPLE

Materials and Methods
Phage Growth and Purification:

Filamentous phages (M13) were prepared from transformed TG1 cultures in 2YT broth, containing 50 µg/ml kanamycin. Bacterial cells were pelleted by centrifugation, and the clarified supernatant was decanted. Phages were precipitated from the supernatant by adding 20% of the original volume of 20% polyethylene glycol (molecular mass 8000 Da) in 2.5M NaCl and standing at 4° C. for 3 hours. Phages were pelleted by centrifugation (9,000 rpm, 1 hour) then resuspended in 3% of the supernatant volume of PBS. Bacterial residues were removed by further centrifugation at 7000 rpm, and the phages were concentrated again by additional polyethylene glycol precipitation. The pellet was finally resuspended in PBS in 0.001 of the original volume of growth media. (Hart et al, 1994).

Phage Interference with β-amyloid Aggregation:

The ability of the phage to prevent βA aggregation and to disaggregate already formed aggregates was analyzed by three approaches:

1. Thioflavin-T Fluorescence assay:

βA aggregation was measured using Thioflavin-T (ThT) dye which changes its emission spectra upon binding to amyloid fibrils (LeVine, 1993). To evaluate phage ability to prevent aggregates formation, 8 µl of βA1-40 577 µM (Bachem), was incubated at 37° C. for 14 days, either alone (diluted to 80 µl with PBS to a final concentration of 58 µM) or with filamentous phage (72 µl of $3\times10^{12}$ phages/ml). The fluorescence of each reaction mixture (20 µl) was measured after addition of 980 µl ThT (2 µM) (Sigma) in 50 mM glycine buffer pH9. Fluorescence was measured using a Perkin-Elmer model LS-50 spectrofluorimeter at an excitation wavelength of 435 nm and an emission wavelength at 485 nm.

Disaggregating activity of the phage was examined as follows: βA (58 µM) was incubated for 21 days at 37° C. to promote aggregation. Phages were added (equal volume of phage of concentration $10^{14}$ phages/ml solution) and incubated with the aggregated βA for another 17 hours. The extent of aggregation was evaluated using ThT fluorescence, as described above.

2. Electron Microscopy (EM):

Interaction of β-amyloid and filamentous phage. Level of βA aggregation was visualized using EM. For the prevention of βA formation, 10 µl of the peptide (289 µM) was incubated either alone (20 µl PBS were added) or in combination with different phage concentrations (20 µl of phage from the following concentrations: $1\times10^{14}$ phages/ml, $1\times10^{12}$ phages/ml, and $1\times10^{10}$ phages/ml) for 9 days at 37° C.

Disaggregating activity of the phage was demonstrated by adding different phage concentrations to preaggregated βA. 20 µl of β-amyloid 1-40 (193 µM) dissolved in PBS were incubated at 37° C. for 10 days. On the $10^{th}$ day, 10 µl of PBS or different phage concentrations ($1\times10^{14}$ phages/ml, $1\times10^{12}$ phages/ml) were added to the sample and incubated for an additional 16 hours.

In both the prevention and disaggregation assays, phages and βA were adhered to carbon evaporated coated formvar 200# grids. Immunolabeling of the amyloid and phages was performed using various sizes of gold-conjugated antibodies (Lin et al., 1999) to distinguish easily between β-amyloid fibrils and phage which may resemble amyloid filaments. β-amyloid fibrils were stained with monoclonal antibody (mAb) 10D5, and $2^{nd}$ antibody goat anti-mouse conjugated to 12 nm gold particles (Electron Microscopy Sciences, Washington, USA). To label the phage, rabbit polyclonal sera against phage was used, and the $2^{nd}$ antibody was conjugated to 6 nm gold particles (Electron Microscopy Sciences). The samples were negatively stained with aqueous (2% wt/vol) uranyl acetate (Sigma). The grids were visualized using JEOL 1200 EX electron microscope at 30K and 100K magnifications.

Interaction of β-amyloid and chloroform treated phages. 200 µl of phages ($10^{14}$ phages/ml) were added to 200 µl chloroform. The solution was vortexed 6 times (10 seconds each) over 3 minute at room temperature (Griffith et al, 1981) The tube was centrifuged at 13,200 rpm for 1 minute; the aqueous phase was transferred to another tube, and left in the hood to evaporate chloroform residues. The interaction between β-amyloid and spherical phages was analyzed by electron microscope.

β-amyloid (97 µM) was incubated at 37° C. for 13 days. On the $13^{th}$ day, PBS or different concentrations of S-phages (chloroform treated) ($5\times10^{13}$ phages/ml, $5\times10^{11}$ phages/ml) were added to the samples and were further incubated for 16 hours. The degree of β-amyloid aggregation was visualized by JEOL 1200 EX electron microscope as was previously described.

3. MTT Assay:

MTT assay was performed to evaluate phage protection from A toxicity on human neuronal cell-line viability. The assay is based on the reduction of 3-(4,5-dimethylthiazol-2-yl)-2,5-diphenyl tetrazolium bromide (MTT) to MTT-formazan in living cells. MTT-formazan concentration was measured by spectrophotometer at 570 nm and is directly correlated to cell viability.

LAN-1 human neuronal cell-line was cultured in RPMI supplemented with 10% fetal calf serum, and 100 units/ml penicillin/streptomycin and incubated at 37° C. under 5% $CO_2$. For the neurotoxicity assay, cultured LAN-1 cells were seeded into a 96-well plate at a density of $10^4$ cells/100 µl/well. The dose-dependent neurotoxicity was measured using samples of β-amyloid (289 µM) either alone or with different phage concentrations.

2 µL of the peptide were incubated with 8 µl of different phage concentrations ($5\times10^{13}$/ml, $5\times10^{12}$/ml, $5\times10^{11}$/ml phages) for 4 days at 37° C. in order to examine phage preventive effect against βA neurotoxicity. The samples were added 24 hours after the cells were seeded and attached to the plate. The plates were incubated at 37° C. for 2 days, after which cell viability was assessed by measuring cellular redox activity with 3-(4,5-dimethylthiazol-2-yl)-2,5-diphenyl tetrazolium bromide (MTT) as was previously described (Solomon et al, 1997). MTT (Sigma) was added to the wells at a final concentration of 1 mg/ml and incubated with the cells for a further 3 hours at 37° C. Cell lysis buffer (20% wt/vol SDS in a solution of 50% dimethylformamide, pH 7.4) was added, and the plate was incubated overnight at 37° C. MTT reduction was determined colorimetrically by the change in OD at 570 nm using an automated microplate spectrophotometer.

In the disaggregation assay of already formed βA fibrils, two peptides were used (β-amyloid 17-42 and β-amyloid 1-40) as the neurotoxic factors. The ability of the phage to protect the cell viability from the aggregated peptides was examined as follows below. In the first experiment, the cells were incubated for 5 days with preaggregated βA 1-40, while in the second experiment, β-amyloid 17-42 was used as the neurotoxic peptide. As was previously described, the cells were seeded into a 96-well plate at a density of $10^4$ cells/100 μl/well and allowed to attach for 24 hours before the samples were added. To 2 μl of the aggregated peptide (288 μM-stock solution), 8 μl of the phages ($10^{14}$ phages/ml, $10^{13}$ phages/ml, $10^{12}$ phages/ml) were added and incubated overnight. The samples were added to the cells, and were further incubated for two days. MTT at a final concentration of 1 mg/ml was added, and lysis buffer was put 3 hours later to enable measurement of MTT-formazan content. Cell viability was assessed by quantifying the O.D. change in 570 nm.

In-vivo Application of Filamentous Phage:

Wild-type, as well as transgenic mice, model of AD were challenged with a filamentous phage:

Evaluation of anti-aggregating properties. In order to assess maximum potential of phage activity as an anti-aggregating agent, phages were injected intracranially to transgenic mice (Taconic, APPSWE(2576), 10 month-old) as follows:

2.5 μl the filamentous phage solution ($10^{14}$ phages/ml) was injected over 10 minutes (Bregma −2.8 mm, lateral 2.5 mm, ventral 2.5 mm) to one hemisphere, while to the contra-lateral side, phosphate-buffer-saline (PBS) was applied as a control (FIG. 1). Since the time period required for phages to disaggregate amyloid deposits is unknown, the treated mice were sacrificed at different time points. The first group was intracardially perfused using 4% paraformaldehyde one hour post-injection, the second group—two days after administration, and the last group—after 3 days. Their brains were post-fixed overnight in 4% paraformaldehyde, and cut using a microtome. Thioflavin-S (ThS) staining was performed to evaluate plaque load. For this purpose, the sections were stained with Mayer's hematoxylin to quench nuclear autofluorescence and after washing, ThS solution (1%) was applied for 3 minutes. Differentiation was done using 1% acetic acid for 20 min, and after washes the slides were dried and mounted with anti fade mounting medium. Plaque load was calculated using LEICA Qwin program.

Biodistribution of radioactive labeling of filamentous phage. Filamentous phages were radioactively labeled with $I^{125}$. The phages were purified from the unbound iodine using G25 sephadex column and the eluate was further precipitated using polyethylene-glycol (PEG) as was previously described. 9 BALB/c mice were divided into 3 groups. Each mouse received intranasally 100 μl of phages ($1.25 \times 10^{12}$ phages) over an hour, labeled with 9 microcurie $I^{125}$. The first group of mice was sacrificed an hour after administration of intra-cardial perfusion using 4% paraformaldehyde. The second group was sacrificed 3 hours post-treatment, and the last group, after 24 hours. After perfusion, the brains as well as the periphery organs were removed and their gamma radiation was measured.

Intranasal administration of filamentous phage. To fully evaluate the effect of filamentous phage, the phages were administered intranasally to SWE/APP2576 transgenic mice (Taconic, 10 month-old). 20 μl of phage solution ($5 \times 10^{12}$/ml) were applied every two weeks, for 4 months and cognitive functions were evaluated. After the ninth immunization, an object recognition test was carried out to study the influence of phage on memory improvement. On the first day, mice were exposed to two new objects for 20 minutes. On the following day, one object was replaced, and the curiosity of the mice to explore the novel item was tested. Recognition index was calculated for each mouse by dividing the time it spent near the new object by the total time it spent near both objects. Thus, values above 0.5 are indicative for recognizing the old item and spending more time around the new object for its investigation.

Results

In vitro anti-aggregating properties of filamentous phages were evaluated regarding reduction and prevention of amyloid formation. In the Thioflavine-T assay, the phages were more efficient in disaggregating βA fibrils than in preventing their formation. A decline of 26% in βA aggregation was observed (FIG. 2B) when the peptide was incubated with filamentous phage in a molar ratio 1:10,000 (phage to βA). Phage addition (28 nM) to preaggregated βA resulted in 45% reduction in amyloid fibrils (FIG. 2A).

Figure 3C:
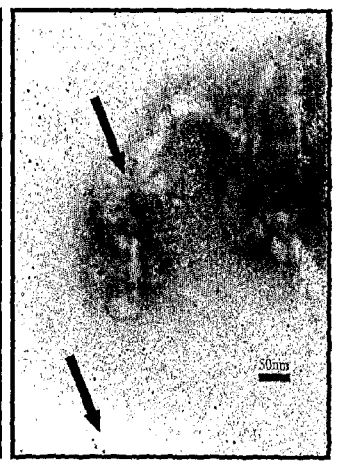
Figure 3D:
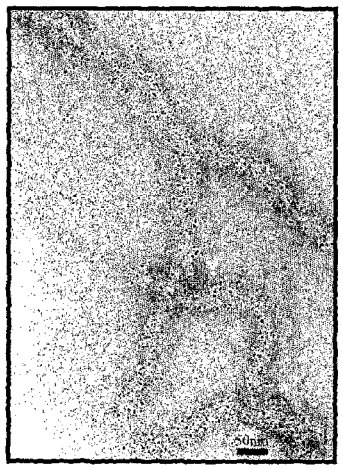
Figure 3E:

Visualization of the physical interaction between phages and β-amyloid peptide by electron microscopy was made using immunogold-stained β-amyloid and its complexes with phages. When phages interact with β-amyloid peptide, the aggregates are smaller and more diffused compared to phage absence. Interestingly, incubation of phages with β-amyloid peptide led to phage degradation, as can be learned from the massive labeling of antibody against phage major coat protein not on phage particles (FIG. 3C). This phenomenon was not observed when the phages were incubated with β-amyloid peptide overnight (in the disaggregation assay) or when phages were incubated alone for the same period of time (FIG. 3D). FIG. 3(F-K) shows the effect of phages on formed amyloid aggregates. FIG. 3F demonstrates amyloid fibrils in a cluster labeled by the 12 nm gold particle. Higher magnification (FIG. 3G) shows the different sizes of aggregated fibril needles. FIGS. 3H-K present phages organized in bundles (arrow head) which are dispersed when attached to the amyloid needles (arrow). The amyloid cluster is small and contains small narrow amyloid fibrils. Of special interest is the parallel organization of the phages to the amyloid fibrils (open arrow).

The pVIII molecule has been shown to exist in three conformations. In the intact phage, the protein is at least 90% α-helical, but large changes in shape occur upon exposure to chloroform/water interface. This is a temperature-dependent process. Rods (I-forms) are formed at 2° C. while spherical structures (S-forms) are formed at 25° C. The conversion to S-form occurs with a substantial decrease in the helix content of the coat protein but with a significant change in the environment of tryptophan 26 (Roberts and Dunker, 1993).

Treatment of the phages with chloroform for three minutes showed that although spherical phages are present at the site of βA aggregates, they are usually located at the end of the fibrils and do not contribute to solubilization (FIGS. 4A-B).

MTT:

Filamentous phage protection on LAN-1 cells from βA neurotoxicity was demonstrated using the MTT assay. When phages were incubated with βA, neuronal viability increased compared to cells that grew in the presence of βA alone. The highest amount of phages that was added to the cell culture caused the most significant effect (17% increase in cell viability) (FIG. 5A).

Figure 5B:
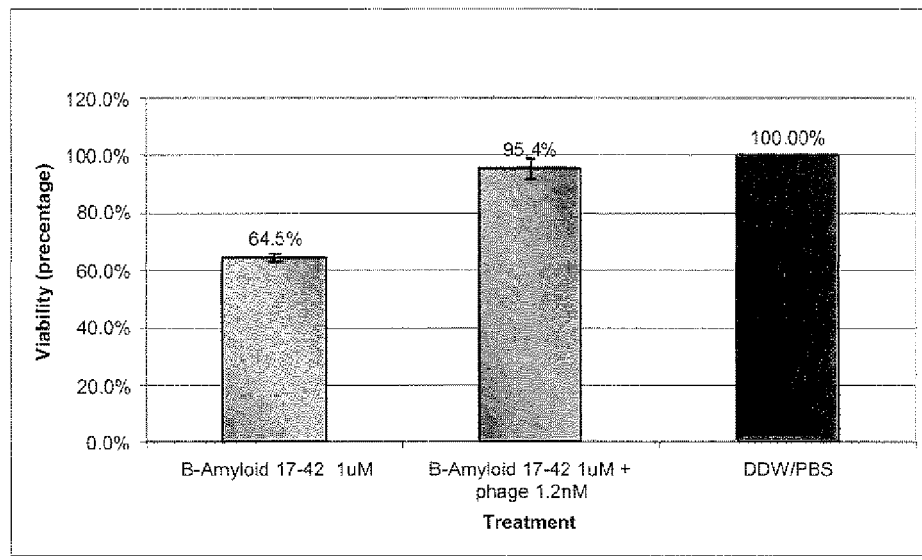
Figure 5C:
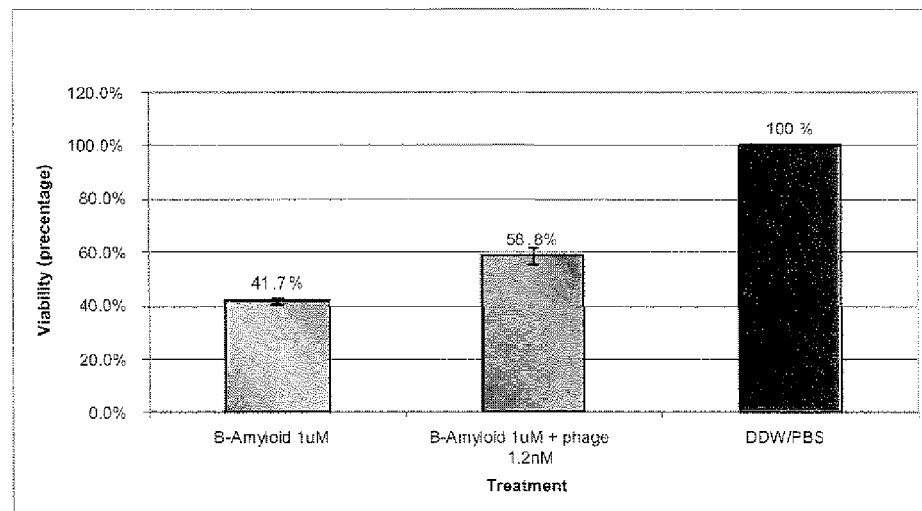

Phage protection from β-amyloid 17-42 toxicity was higher compared to its ability to prevent β-amyloid 1-40 toxicity. When phages were added to the preaggregated βA 17-42, cell viability was increased by 30%, compared to cells that grew with βA alone (FIG. 5B). Addition of the same phage concentration to βA 1-40 resulted in only 17% increase in cell viability (FIG. 5C). Addition of higher concentration of phages succeeded to increase cell viability to 25% compared to βA treated cells.

A possible reason for this difference could be attributed to the N-terminus of β-amyloid that may interfere with phage activity, or due to the fact that β-amyloid 17-42 aggregates faster than β-amyloid 1-40 (Pike et al., 1995). Phage affinity to β-amyloid 1-40 increases with the peptide aggregation. ELISA, which checked phage binding to soluble β-amyloid, 1 hour aggregated β-amyloid or 3 weeks aggregated peptide, showed significant difference in phage binding to βA 1-40. Therefore the higher affinity of phages to the highly aggregated peptide may explain its stronger interactions with β-amyloid 17-42.

Figure 6A:
FIGS. 6A and 6B show filamentous phage injected into one hemisphere of hAPP transgenic mice (SWE2576, Taconic) (FIG. 6B) and PBS alone injected into the other hemisphere (FIG. 6A). Mice that were sacrificed 3 days post treatment showed 40% reduction in plaque load, compared to the PBS treated hemisphere.
Figure 6B:
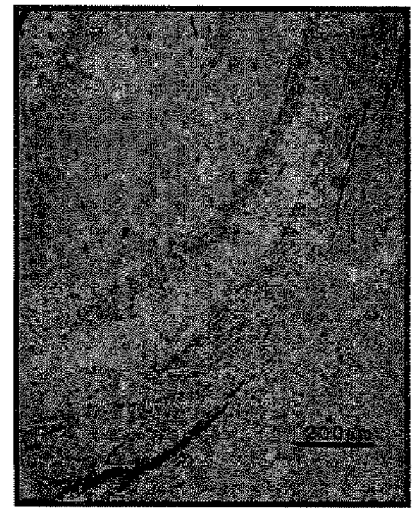

In the in-vivo studies of disaggregation of β-amyloid plaques by intracerebral injection of filamentous phages, no reduction in plaque load was detected in mice sacrificed one hour post injection. In mice sacrificed two days after treatment, 25% reduction in plague load was noticed in the hemisphere treated with filamentous phage compared to PBS injected hemisphere. Mice sacrificed three days after treatment showed 40% reduction in plaque load in the phage-injected hemisphere (FIGS. 6A and 6B).

Figure 7:
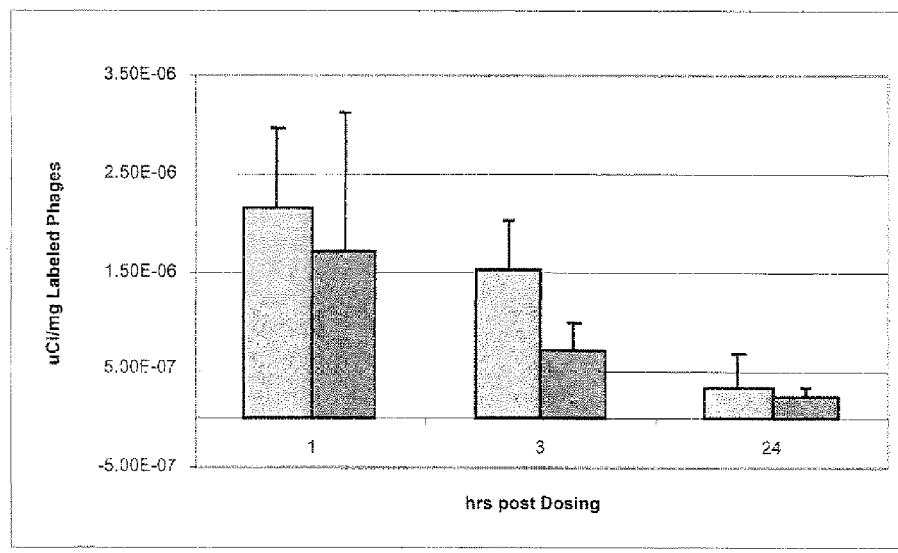
FIG. 7 is a graph showing the phage distribution in BALB/c mice after intranasal application. Comparison between phage distribution in the brain and olfactory bulb 1, 3, and 24 hours post nasal administration to BALB/c mice showed phage presence (labeled phages in uCi/mg) even one hour after administration. Their concentration was reduced after this one hour time point.

Brain Distribution of Radioactive Labeled Filamentous Phages:

Following intranasal administration, filamentous phages were detected in the olfactory bulb and in the brain as early as 1 hour post administration (FIG. 7). Although the groups were too small (n=3) to conclude phage clearance rate, it seems that phage concentration reaches its peak after an hour, and is then eliminated almost completely within 24 hours. The high variability between the mice can be the result of swallowing and inhaling different amounts of phages. The penetrated dose to brain parenchyma varied from 0.0009% to 0.018% of the given dose. It is worth mentioning that 0.1% of antibody sera concentration succeeded in reaching the brain and reduce plaque load. These preliminary data show that phage can penetrate the brain in a short time and start clearance after an hour in normal BALB/C mice. Therefore, intranasal administration of filamentous phage can be tested for its efficiency in treating transgenic mice bearing amyloid deposits.

Repeated Intranasal Administration of Filamentous Phage into Transgenic Mice:

Significant improvement in cognitive functions was noticed in the phage-treated mice compared to the non-treated group (data not shown). At the end of the study, histochemical analysis will be performed to evaluate mice plaque load, microglia activation, synapses density and probable adverse effects in order to get a comprehensive estimation of treatment efficiency.

Discussion

The laboratory of the present inventors have previously reported that site-directed monoclonal antibodies (mAbs) towards the N-terminal region of βa, bind preformed βA fibrils, and lead to amyloid disaggregation into an amorphous state and inhibit their neurotoxic effect (Solomon et al., 1996, 1997). This activity was also demonstrated in vivo in transgenic mice for AD (Bard et al., 2000). Phage displaying scFv against βA to deliver intranasally anti-aggregating antibody fragment to brain plaques was used (Frenkel et al., 2002). The phage was used as a vehicle which enabled scFv penetration to the brain and its binding to amyloid deposits in transgenic mice.

A direct correlation was shown between the number of applications and the amount of phage detected in the hippocampus and olfactory bulb. The linear structure of the phage is suggested to confer penetration properties via various membranes. It is worth mentioning that no pathological signs were observed in those mice brains after phage administration (Frenkel et al., 2002).

βA fibrils were visualized both by ThT and fluorescent labeled anti-phage antibodies and the disappearance of filamentous phage from the brain without inducing toxic effect was shown in histology studies. In previously reported experiments, filamentous phages were intravenously injected into mice and were subsequently rescued from the difference organs, showing that their integrity was not affected during circulation in the body.

Amyloid fibrillization is considered to be driven by hydrophobic rather than electrostatic interactions. βA contains two hydrophobic segments, the central part of which is composed of residues 17-21 and the C-terminal region that contains residues 30-40. According to the model based on experimental constraints from solid state NMR, the peptide conformation contains two β-strands, separated by a 180° bend formed by residues 25-29. The β-strands form two in-register parallel β-sheets, which interact through sidechain-sidechain contacts. The hydrophobic sidechains are exposed to the outer surface and form a hydrophobic face, while the other charged and polar sidechains are distributed on the opposite face, on the convex side of the bend, and in the N-terminal segment where they could be solvated as the fibrils grow (Petkova et al, 2002).

On the other hand, the major phage coat protein is composed from three sections: the outer surface, occupied by the N-terminal region of the subunit, rich in acidic residues that interact with the surrounding solvent and give the virion a low isoelectric point; the interior of the shell, including a 19-residue stretch of apolar side-chains, where protein subunits interact mainly with each other; and the inner surface, occupied by the C-terminal region of the subunit, rich in basic residues that interact with the DNA core. The fact that virtually all protein side-chain interactions are between different subunits in the coat protein array, rather than within subunits, makes this a useful model system for studies of the interactions between α-helix subunits in a macromolecular assembly.

In the present study, it was demonstrated that phages possess anti-aggregating properties in addition to its reported function as a vehicle for delivering antibodies against βA to the brain. From the data presented in the Example, filamentous phage interacts with β-amyloid and can interfere with its aggregation process and even induce its solubilization. Disaggregating property is of great value since, at present, diagnosis is made in late stages of the disease when β-amyloid plaques are already formed. This process is time dependent since after intracranial injection of phages into Tg mice bearing amyloid plaques, maximum effect was observed only after 3 days. This effect can be the result of the phage's unique structure as a long thin filament which enables it to organize along the amyloid fibrils, as can be seen in the electron microscopy micrographs. This theory is evidenced by the fact that spherical phages which lost their linear structure could not inhibit amyloid formation. Another factor that can be a major contributor to phage activity is its high content of alpha-helices (protein 8) which may interfere with beta sheet structure. The pVIII subunits pack in a helical array to form a tubular structure which surrounds the ssDNA genome. The C-terminal end of pVIII is exposed towards the inside of the tubular structure and contains positively charged residues which interact with the negatively charged ssDNA genome. The middle portion is rich in hydrophobic amino acids which are responsible for the interaction among subunits. Finally, the flexible, negatively charged N-terminal portion is exposed to the outside of the particle (Marvin, 1998).

Filamentous bacteriophages offer an obvious advantage over other vectors. The filamentous phages, M13, f1, and fd, are well understood at both structural and genetic levels (Wilson and Finley 1998; Rodi and Makowski, 1999). They were genetically engineered to display both antigen and/or antibody and were used in different biological systems to present foreign proteins on their surfaces (Scott et al. 1990; McCafferty et al 1990). Having evolved for prokaryotic infection, assembly and replication, bacteriophage can neither replicate in, nor show natural tropism for mammalian cells. This minimizes the chances of non-specific gene delivery. Phage vectors are potentially much safer than other viruses, as they are less likely to generate a replication-competent entity in animal cells.

Another benefit in using bacteriophage as disaggregating agent is its easy production, since more material can be easily obtained by growth of bacterial cultures. According to the radioactive labeling assay, phage penetrate to brain parenchyma after less than an hour. Their elimination probably begins soon after. The percentage of the penetrated phage from the administered dose varied from 0.0009% to 0.018%. More studies should be performed to minimize the variability between the mice. Minimizing the dose, and waiting longer between each drop can help. In comparison, 0.1% from antibody sera concentration reaches the brain. Although the molecular weight of the phage is two orders of magnitude higher than antibody, intranasal application can result in phage penetration.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Banks and Kastin, *Prog Brain Res.*, 91:139-4 (1992)

Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T. Peripherally administered antibodies against amyloid beta-peptide enter the central nervous system and reduce pathology in a mouse model of Alzheimer disease. *Nat Med. August;* 6(8):916-9 (2000)

Caughey et al, "Secondary structure analysis of the scrapie-associated protein PrP 27-30 in water by infrared spectroscopy", *Biochemistry* 30:7672-7680 (1991)

Chartier Harlan et al, *Nature* 353:844 (1991)

Chou et al, *Biopharm Drug Dispos.* 18(4):335-46 (1997)

De Gioia et al, "Conformational polymorphism of the amyloidogenic and neurotoxic peptide homologous to residues 106-126 of the prion protein", *J Biol Chem* 269:7859-7862 (1994)

Draghia et al, *Gene Therapy* 2:418-423 (1995)

Forloni et al, "Neurotoxicity of a prion protein fragment", *Nature* 362:543-546 (1993)

Frenkel and Solomon, *PNAS,* 99:5675-5679 (2002)

Frenkel D, Solomon B. Filamentous phage as vector-mediated antibody delivery to the brain. *Proc Natl Acad Sci USA*. April 16; 99(8):5675-9 (2002)

Frenkel et al, "N-terminal EFRH sequence of Alzheimer's β-amyloid peptide represents the epitope of its anti-aggregating antibodies", *J Neuroimmunology* 88:85-90 (1998)

Gajdusek, *Science* 197:943-960 (1991)

Gazit E., Mechanistic studies of the process of amyloid fibrils formation by the use of peptide fragments and analogues: implications for the design of fibrillization inhibitors. *Curr Med Chem*. October; 9(19):1725-35 2002

Goate et al, *Nature* 349:704 (1991)

Greenwood et al., *J. Mol. Biol.,* 220:821-827 (1991)

Griffith J., Manning N., Dunn K, Filamentous bacteriophage contract into hollow spherical particles upon exposure to a chloroform-water interface. *Cell.* March; 23(3):747-53 (1981)

Hardy, *TINS,* 20:154 (1997)

Hart S L, Knight A M, Harbottle R P, Mistry A, Hunger H D, Cutler D F, Williamson R, Coutelle C. Cell binding and internalization by filamentous phage displaying a cyclic Arg-Gly-Asp-containing peptide. *J Biol Chem*. April 29; 269(17):12468-74 (1994)

Horiuchi and Caughey, "Specific binding of normal prion protein to the scrapie form via a localized domain initiates its conversion to the protease-resistant state", *EMBO J.* 18:3193-3203 (1999)

Kanyo et al, "Antibody binding defines a structure for an epitope that participates in the PrPC—>PrPSc conformational change", *J Mol. Biol.* 293:855-863 (1999)

LeVine H 3rd, Thioflavine T interaction with synthetic Alzheimer's disease beta-amyloid peptides: detection of amyloid aggregation in solution. *Protein Sci.* March; 2(3):404-10 (1993)

Lin J. Yanase K, Rutgers A, Madaio M P, Meyers K B, Selection of specific phage from display libraries: monoclonal antibody against VCS M13 helper phage coat protein III (gIIIp). *Hybridoma*, June; 18(3):257-61 (1999)

Maggio J E, Mantyh P W, Brain amyloid—a physicochemical perspective. *Brain Pathol.* April; 6(2):147-62 (1996)

Marvin D A, Hale R D, Nave C, Citterich M H, Molecular models and structural comparisons of native and mutant class I filamentous bacteriophages Ff (fd, f1, M13), If1 and Ike. *J. Mol. Biol.* 235:260-286 (1994)

Marvin D A. Filamentous phage structure, infection and assembly. *Curr Opin Struct Biol.* April; 8(2):150-8 (1998)

Mathison at al, *J. Drug Target,* 5(6):415-441 (1998)

McCafferty J, Griffiths A D, Winter G, Chiswell D J. Phage antibodies: filamentous phage displaying antibody variable domains. *Nature.* December 6; 348(6301):552-4 (1990)

Medori, Tritschler et al., *N Engl J Med* 326: 444-449 (1992)

Monaci P., et al., *Curr Opin Mol Ther.,* 3(2):159-69 (2001)

Mullan et al, *Nature Genet.* 1:345 (1992)

Murrell et al, *Science* 254:97 (1991)

Pan et al, "Conversion of alpha-helices into beta-sheets features in the formation of the scrapie prion proteins", *Proc Natl Aced Sci USA* 90:10962-10966 (1993)

Peretz et al, "A conformational transition at the N terminus of the prion protein features in formation of the scrapie isoform", *J Mol Biol* 273:614-622 (1997)

Pike C J, Overman M. J, Cotman C. W, Amino-terminal deletions enhance aggregation of beta-amyloid peptides in vitro. *J Biol. Chem.* October 13; 270(41):23895-8 (1995)

Roberts L M, Dunker A K, Structural changes accompanying chloroform-induced contraction of the filamentous phage fd. *Biochemistry.* October 5; 32(39):10479-88 (1993)

Rodi, D J. and Makowski, L., Phage-display technology—finding a needle in a vast molecular haystack. *Curr. Opin. Biotechnol.,* 10:87-93 (1999)

Scott, J K.; and Smith, G P, Searching for peptide ligands with an epitope library. Science, 249: 386-390 (1990)

Selvaggini et al, "Molecular characteristics of a protease-resistant, amyloidogenic and neurotoxic peptide homologous to residues 106-126 of the prion protein", *Biochem Biophys Res Commun* 194:1380-1386 (1993)

Silen and Agard, "The alpha-lytic protease pro-region does not require a physical linkage to activate the protease domain in vivo", *Nature* 341:462-464 (1989)

Solomon B, Koppel R, Frankel D, Hanan-Aharon E., Disaggregation of Alzheimer beta-amyloid by site-directed mAb. *Proc Natl Acad Sci USA.* April 15; 94(8):4109-12 (1997)

Solomon B, Koppel R, Hanan E, Katzav T., Monoclonal antibodies inhibit in vitro fibrillar aggregation of the Alzheimer beta-amyloid peptide. *Proc Natl Acad Sci USA.* January 9; 93(1):452-5 (1996)

Tagliavini et al, "Synthetic peptides homologous to prion protein residues 106-147 form amyloid-like fibrils in vitro", *Proc Natl Acad Sci USA* 90:9678-9682 (1993)

Wilesmith and Wells, *Curr Top Microbiol Immunol* 172:21-38 (1991)

Wilson, D R. and Finlay, B B., Phage display: applications, innovations, and issues in phage and host biology. *Can. J. Microbiol.* 44: 313-329 (1998)

Young A A. et al, *FEES Lett,* 343(3):237-41 (1994)

What is claimed is:

1. A pharmaceutical composition comprising a filamentous bacteriophage and a pharmaceutically acceptable carrier or excipient, wherein:
   substantially all of the filamentous bacteriophage in the composition consists of a non-radioactively labeled filamentous bacteriophage which does not display an antibody and does not display a non-filamentous bacteriophage antigen on its surface; and
   the composition is in unit dosage form.

2. The pharmaceutical composition of claim 1, wherein the filamentous bacteriophage is selected from the group consisting of M13, f1, fd, and mixtures thereof.

3. The pharmaceutical composition of claim 2, wherein the filamentous bacteriophage is a wild-type M13 bacteriophage.

4. The pharmaceutical composition of claim 1, wherein the non-radioactively labeled filamentous bacteriophage is a non-radioactively labeled wild-type filamentous bacteriophage.

5. A pharmaceutical composition consisting essentially of a filamentous bacteriophage and a pharmaceutically acceptable carrier or excipient, wherein:
   the filamentous bacteriophage in the composition consists of a non-radioactively labeled filamentous bacteriophage which does not display an antibody and does not display a non-filamentous bacteriophage antigen on its surface; and
   the composition is in unit dosage form.

6. The pharmaceutical composition of claim 5, wherein the filamentous bacteriophage is selected from the group consisting of M13, f1, fd, and mixtures thereof.

7. The pharmaceutical composition of claim 6, wherein the filamentous bacteriophage is a wild-type M13 bacteriophage.

8. The pharmaceutical composition of claim 5, wherein the non-radioactively labeled filamentous bacteriophage is a non-radioactively labeled wild-type filamentous bacteriophage.

9. A method for reducing the amount of fibrillar amyloid plaque in a subject suffering from a plaque forming disease, comprising administering to the subject in need thereof an amount of a filamentous bacteriophage which does not display an antibody or a non-filamentous bacteriophage antigen on its surface effective to reduce the amount of fibrillar amyloid plaque in the subject and by a route of administration that causes the bacteriophage to come into contact with the fibrillar amyloid plaque.

10. The method of claim 9, wherein the plaque forming disease is selected from the group consisting of early onset Alzheimer's disease, late onset Alzheimer's disease, presymptomatic Alzheimer's disease, SAA amyloidosis, hereditary Icelandic syndrome, senility, multiple myeloma, kuru, Creutzfeldt-Jakob disease (CJD), Gerstmann-Straussler-Scheinker disease (GSS), fatal familial insomnia (FFI), scrapie, bovine spongiform encephalitis (BSE), and other diseases characterized by formation of fibrillar amyloid plaques by an aggregating protein selected from the group consisting of beta-amyloid, serum amyloid A, cystatin C, IgG kappa light chain and prion protein.

11. The method of claim 8, wherein the filamentous bacteriophage is administered by a route of administration that causes the bacteriophage to come into contact with fibrillar amyloid plaque present in the brain of the subject.

12. The method of claim 11, wherein the route of administration is intrathecal or direct intraventricular.

13. The method to claim 12, wherein the administration is by bolus injection or continuous infusion.

14. The method of claim 9, wherein the plaque forming disease is selected from the group consisting of early onset Alzheimer's disease, late onset Alzheimer's disease, presymptomatic Alzheimer's disease, kuru, Creutzfeldt-Jakob disease (CJD), Gerstmann-Straussler-Scheinker disease (GSS), fatal familial insomnia (FFI), scrapie, bovine spongiform encephalitis (BSE), and other diseases characterized by formation of fibrillar amyloid plaques by an aggregating protein selected from the group consisting of beta-amyloid and prion protein.

15. The method of claim 9, wherein the plaque forming disease is selected from the group consisting of early onset Alzheimer's disease, late onset Alzheimer's disease and presymptomatic Alzheimer's disease.

16. The method of claim 9, wherein the filamentous bacteriophage is a wild-type filamentous bacteriophage.

* * * * *